US010196378B2

(12) United States Patent
Soellner et al.

(10) Patent No.: US 10,196,378 B2
(45) Date of Patent: Feb. 5, 2019

(54) INHIBITORS OF BCR-ABL MUTANTS AND USE THEREOF

(71) Applicant: THE REGENTS OF THE UNIVERSITY OF MICHIGAN, Ann Arbor, MI (US)

(72) Inventors: Matthew B. Soellner, Dexter, MI (US); Sameer Phadke, Mumbai (IN)

(73) Assignee: THE REGENTS OF THE UNIVERSITY OF MICHIGAN, Ann Arbor, MI (US)

(*) Notice: Subject to any disclaimer, the term of this patent is extended or adjusted under 35 U.S.C. 154(b) by 0 days.

(21) Appl. No.: 15/685,707

(22) Filed: Aug. 24, 2017

(65) Prior Publication Data
US 2018/0057479 A1 Mar. 1, 2018

Related U.S. Application Data

(60) Provisional application No. 62/379,499, filed on Aug. 25, 2016.

(51) Int. Cl.
| C07D 401/14 | (2006.01) |
| C07D 213/68 | (2006.01) |
| C07D 213/81 | (2006.01) |
| C07D 215/20 | (2006.01) |
| C07D 215/38 | (2006.01) |
| C07D 239/74 | (2006.01) |
| C07D 295/135 | (2006.01) |
| A61K 31/44 | (2006.01) |
| A61K 31/444 | (2006.01) |

(52) U.S. Cl.
CPC ......... *C07D 401/14* (2013.01); *C07D 213/68* (2013.01); *C07D 213/81* (2013.01); *C07D 215/20* (2013.01); *C07D 215/38* (2013.01); *C07D 239/74* (2013.01); *C07D 295/135* (2013.01)

(58) Field of Classification Search
CPC .. C07D 401/14; C07D 239/74; C07D 215/20; C07D 215/38; C07D 213/68; C07D 213/81; C07D 295/135
See application file for complete search history.

(56) References Cited

U.S. PATENT DOCUMENTS

2007/0161677 A1  7/2007  Buchstaller
2009/0124633 A1  5/2009  Jonczyk et al.

FOREIGN PATENT DOCUMENTS

WO   WO-2006071940 A2 * 7/2006 ........... C07D 209/46
WO   WO-2007004749 A1 * 1/2007 ........... C07D 487/04

OTHER PUBLICATIONS

Gainor, J.F., "Ponatinib: accelerated disapproval." (2015): 847-848.*
Verweij, M. F., Preventive medicine between obligation and aspiration. vol. 4. Springer Science & Business Media, 2000.*
CAS Registry Entries, Chemical Abstracts Service 2018, p. 1-2.*
Li, Y., "AutoT&T v. 2: an efficient and versatile tool for lead structure generation and optimization." Journal of chemical information and modeling 56.2 (2016): 435-453.*
PubChem, Substance Record for SID 261424221, dated Dec. 10, 2015. (retrieved from https://pubchem.ncbi.nlm.nih.gov/substance/261424221).
International Search Report and Written Opinion issued in connection with PCT/US17/48441, dated Dec. 20, 2017.

* cited by examiner

*Primary Examiner* — John M Mauro
(74) *Attorney, Agent, or Firm* — Marshall, Gerstein & Borun LLP

(57) ABSTRACT

Inhibitor compounds of Bcr-Abl and Bcr-Abl mutants including Bcr-Abl T315I mutant protein are disclosed. Compositions comprising the inhibitor compounds and methods of using the compounds in the treatment of leukemia such as chronic myelogenous leukemia are also disclosed.

19 Claims, No Drawings

INHIBITORS OF BCR-ABL MUTANTS AND USE THEREOF

CROSS-REFERENCE TO RELATED APPLICATIONS

This application claims priority to U.S. Provisional Patent Application No. 62/379,499, filed on Aug. 25, 2016, the entire contents of which are incorporated by reference.

FIELD OF THE DISCLOSURE

The present disclosure relates to inhibitors of Bcr-Abl and Bcr-Abl mutant proteins including Bcr-Abl T315I mutant protein, and use of the inhibitors as, e.g., therapeutic agents.

BACKGROUND

Aberrant signaling of protein kinases has been implicated in a variety of cancers. A prototypical example of a cancer caused by dysregulated kinase activity is chronic myelogenous leukemia (CML). The reciprocal translocation t(9;22) (q34;q11) of the Abl1 gene on chromosome 9 with part of the Bcr gene on chromosome 22 leads to a fusion protein, Bcr-Abl. An important auto-inhibitory myristoylation site, typically present on wild-type c-Abl, is lost upon forming the fusion protein. Bcr-Abl therefore possesses constitutive kinase activity and is the primary driver for CML.

The development of protein kinase inhibitors for use in oncology was spurred by the success of imatinib, which was approved for the treatment of CML in 2001. In clinical trials, imatinib showed remarkable efficacy in treating CML patients, increasing the 5-year overall survival rate from about 30% (prior to any targeted therapy) to an unprecedented 90%. However, long term treatment with imatinib invariably led to the development of resistance, due to point mutations in its target protein, Bcr-Abl.

Second-generation Bcr-Abl inhibitors nilotinib, dasatinib, and bosutinib were initially approved to counter imatinib-resistant CML. Since then, nilotinib and dasatinib have been approved for front-line CML therapy, while bosutinib is currently approved only for salvage therapy. Each of the four approved Abl inhibitors orthosterically compete with ATP to form hydrogen bonds with the hinge region of c-Abl (i.e. the loop that connects the N- and C-lobes of the kinase). Additionally, the highly-dynamic, glycine-rich, phosphate-binding loop (P-loop) of the kinase makes extensive van der Waals contacts with the hinge-binding motifs of these inhibitors. Dasatinib and bosutinib are termed type-I inhibitors and bind to a conformation of the kinase that closely mimics nucleotide-binding. This conformation, consisting of the activation loop residue D381 (of the DFG motif) positioned for catalysis and the adjacent F382 residue buried in a hydrophobic pocket, is termed the DFG-in active conformation. On the other hand, imatinib and nilotinib, classified as type-II inhibitors, bind to c-Abl in a DFG-out inactive conformation. In this conformation, the inhibitors extend past a so-called 'gatekeeper' residue (T315) into the allosteric hydrophobic pocket normally occupied by F382. Access to the allosteric pocket is facilitated by a 180° flip in the DGF motif.

Point mutations in the kinase domain of c-Abl inhibit binding of imatinib, either through direct or allosteric mechanisms. Over 50 single-point mutations have been identified in various positions of the kinase. The P-loop residues (G250, Y253, E255), gatekeeper residue T315, and the M351 and F359 residues account for over 70% of all mutated residues. The second generation inhibitors are effective against many P-loop mutants of c-Abl, however, like imatinib, they are completely ineffective against the T315I gatekeeper mutation. This specific mutation is the single most common mutation observed and greatly enhances kinase activity. The exact mechanism by which the T315I mutation abrogates binding of first and generation inhibitors is still a debated question. However, it is believed to be, at least in part, due to the elimination of a critical H-bond between the inhibitor and the hydroxyl group of the T315 residue.

Ponatinib, a third-generation type-II inhibitor, is the only drug approved for the treatment of refractory CML caused by T315I Bcr-Abl. Its use, however, has been complicated by its serious vascular adverse events (AEs). In a phase I trial, after a median follow-up of 2.7 years, 48% of patients had experienced serious vascular AEs, loss of blood flow and severe narrowing of blood vessels in the extremities, heart, and brain requiring urgent surgical procedures to restore blood flow. Twenty-seven percent of patients developed arterial or venous thrombosis and occlusions, while heart failure, including fatalities, occurred in 8% of patients. These AEs were found to be both cumulative and dose-dependent resulting in ponatinib being pulled off the market for a short time before being reinstated with a black-box warning.

Imatinib set the bench mark for Bcr-Abl inhibitors not only in its efficacy, but also in its excellent safety profile. The clinical safety of imatinib has been attributed to its narrow spectrum of selectivity. While second generation inhibitors are more promiscuous and show limited AEs, their safety profiles are superior to that of ponatinib. The exact molecular mechanism for the vascular AEs in ponatinib-treated patients is currently unknown, however, it has been correlated with its broad spectrum of selectivity. Particularly, the ability of ponatinib to potently inhibit VEGFR 1-3 (receptors kinases involved in vasculogenesis and angiogenesis) has been hypothesized to cause vascular toxicity. Additionally, ponatinib inhibition of the FGFR kinases is believed to enhance such AEs.

The success of imatinib-therapy has paradoxically led to an increase in the number of patients with CML. Because patients with CML must continue kinase inhibitor therapy for the rest of their lives, an increasing number of these patients will eventually develop resistance to imatinib. Because the median age of patients with CML is >60 years, in whom cardiovascular disease is prevalent, the safety of novel inhibitors of imatinib-resistant CML is critical.

SUMMARY

The present disclosure is directed to Bcr-Abl kinase inhibitors, including Bcr-Abl mutant protein kinase inhibitors, e.g., Bcr-Abl T315I mutant protein. The present disclosure is also directed to use of the inhibitor compounds as therapeutic agents, e.g., to treat leukemia such as chronic myelogenous leukemia (CML).

In one aspect, the present disclosure provides a compound of Formula (I), or a pharmaceutically acceptable salt thereof:

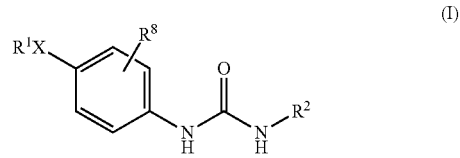

wherein: X is O, NH, or S; $R^1$ is pyridinyl, a fused bicyclic heteroaryl ring system of 9 or 10 atoms, or naphthyl, each of which is unsubstituted or substituted with 1, 2, or 3 independently selected $R^3$ groups; $R^2$ is

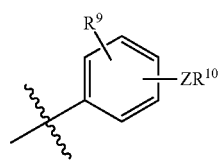

or AR⁶; $R^3$ is halo, $C_{1-5}$ alkyl, $C_{1-5}$ haloalkyl, $CONH_2$, $CONHC_{1-5}$ alkyl, or $NHCOC_{1-5}$ alkyl; A is a heterocycloalkyl or heteroaryl ring system of 5 atoms, which is substituted with $R^5$; $R^5$ is H, $C_{3-5}$ alkyl, or $CF_3$; $R^6$ is phenyl, pyridinyl, a fused bicyclic heteroaryl ring system of 9 or 10 atoms, naphthyl, or a fused bicyclic heterocycloalkyl ring system of 9 or 10 atoms, each of which is unsubstituted or substituted with 1, 2, or 3 independently selected $R^7$ groups; $R^7$ is halo, $C_{1-5}$ alkyl, $C_{1-5}$haloalkyl, $CONH_2$, $CONHC_{1-5}$ alkyl, or $NHCOC_{1-5}$ alkyl; $R^8$ is H, halo, or $C_{1-5}$ alkyl; $R^9$ is H or $CF_3$; Z is null or $CH_2$; $R^{10}$ is a heterocycloalkyl or heteroaryl ring system of 5 or 6 atoms, which is substituted with $R^4$; and $R^4$ is H or $C_{1-3}$ alkyl. In some aspects, the compound of Formula (I) is not

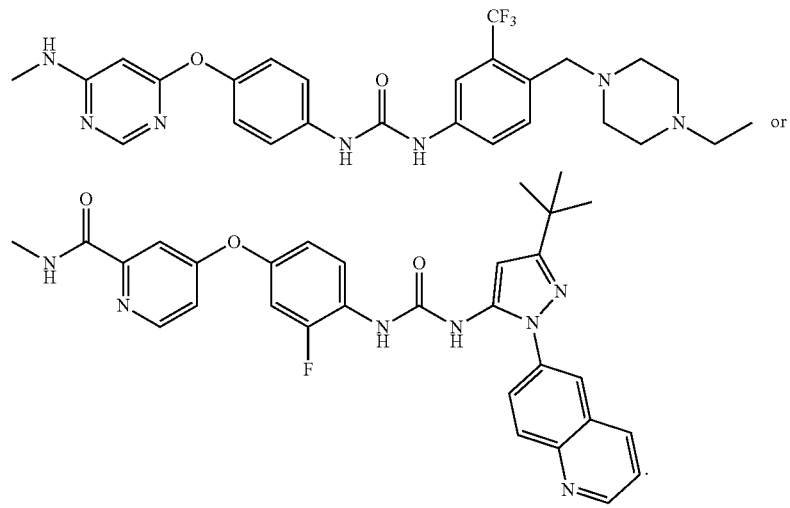

In some aspects, the compound is selected from the group consisting of

C01

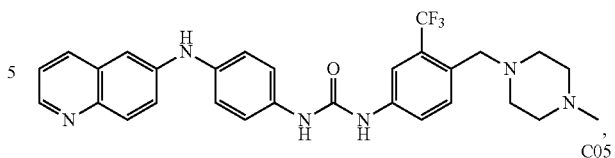

C02

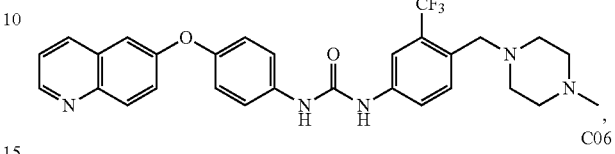

C03

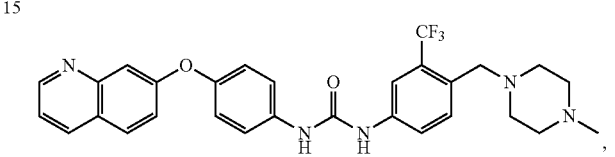

-continued

C04

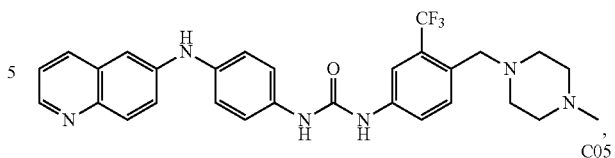

C05

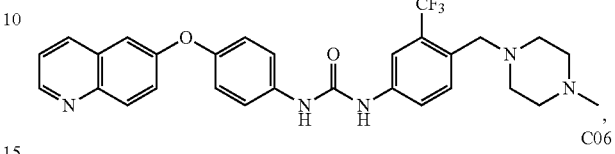

C06

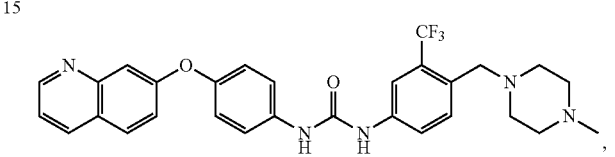

-continued

C07

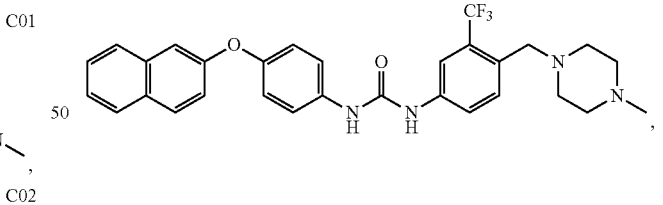

C08

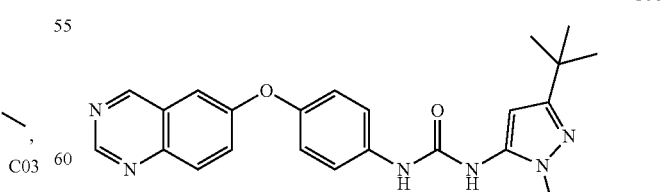

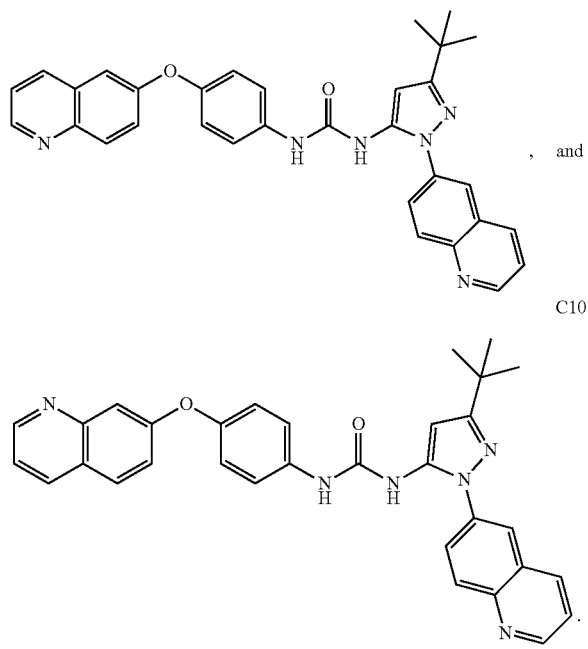

C09

, and

C10

In another aspect, the present disclosure provides a composition comprising a compound described herein, for example, any of compounds C01 to C10 or a combination thereof, and a pharmaceutically acceptable carrier.

In one aspect, the present disclosure provides a method of treating or preventing a hyperproliferative disorder in a subject in need thereof comprising administering a therapeutically effective amount of a compound disclosed herein. In another aspect, the present disclosure provides a method of inhibiting cancer growth or metastasis comprising contacting a cancer cell with an effective amount of a compound disclosed herein. In still another aspect, the present disclosure provides a method of treating cancer in a subject in need thereof comprising administering a therapeutically effective amount of a compound disclosed herein. In any of the methods described herein, the compound is, for example, a compound of Formulae (I), (II), or (III), any one of compounds C01 to C10, or a combination thereof. The methods of the present disclosure may be used to treat a cancer selected from a leukemia such as chronic myelogenous leukemia.

The foregoing summary is not intended to define every aspect of the invention, and other features and advantages of the present disclosure will become apparent from the following detailed description. The present disclosure is intended to be related as a unified document, and it should be understood that all combinations of features described herein are contemplated, even if the combination of features are not found together in the same sentence, paragraph, or section of this disclosure. In addition, the disclosure includes, as an additional aspect, all embodiments of the invention narrower in scope in any way than the variations specifically mentioned above. With respect to aspects of the disclosure described or claimed with "a" or "an," it should be understood that these terms mean "one or more" unless context unambiguously requires a more restricted meaning. With respect to elements described as one or more within a set, it should be understood that all combinations within the set are contemplated. If aspects of the disclosure are described as "comprising" a feature, embodiments also are contemplated "consisting of" or "consisting essentially of" the feature. Additional features and variations of the disclosure will be apparent to those skilled in the art from the entirety of this application, and all such features are intended as aspects of the disclosure.

DETAILED DESCRIPTION

The present disclosure provides Bcr-Abl kinase inhibitors, including Bcr-Abl mutant protein kinase inhibitors, e.g., Bcr-Abl T315I mutant protein. Unlike other kinase inhibitors in clinical use such as ponatinib, the compounds described herein are more selective kinase inhibitors and less prone to exhibiting the vascular toxicity associated with ponatinib.

Ponatinib contains a hinge-binding head group for binding to the hinge region of c-Abl, a linker, and a tail. As shown in Scheme 1, AST-487 (an inhibitor of RET) and rebastinib (a TIE-2 kinase inhibitor), also include head group, linker, and tail motifs. Compared to ponatinib, AST-487 and compounds disclosed herein use a structurally different linker to connect the head group to the tail (apara-disubstituted phenyl linker vs. a meta-substituted phenylalkyne). Further, while some compounds disclosed herein use the tail motif present in ponatinib, rebastinib and other compounds disclosed herein use a structurally different tail motif (a t-butylpyrazolylquinoline tail vs. a trifluoromethylbenzylpiperazine tail).

Scheme 1

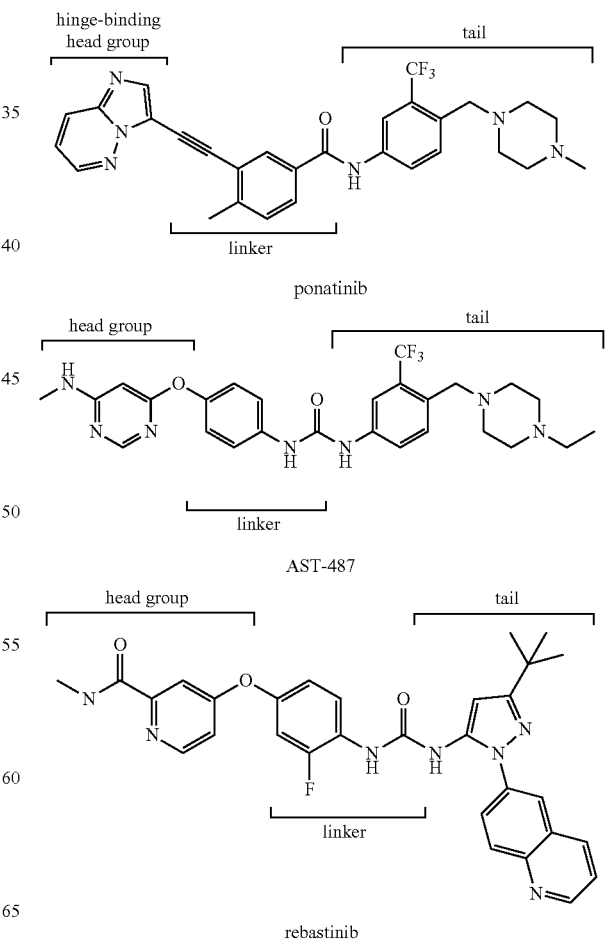

The following definitions may be useful in aiding the skilled practitioner in understanding the disclosure. Unless otherwise defined herein, scientific and technical terms used in the present disclosure shall have the meanings that are commonly understood by those of ordinary skill in the art.

As used herein, the term "alkyl" refers to straight chained and branched saturated hydrocarbon groups containing one to thirty carbon atoms, for example, one to twenty carbon atoms, or one to ten carbon atoms. The term $C_n$ means the alkyl group has "n" carbon atoms. For example, $C_4$ alkyl refers to an alkyl group that has 4 carbon atoms. $C_{1-7}$ alkyl refers to an alkyl group having a number of carbon atoms encompassing the entire range (i.e., 1 to 7 carbon atoms), as well as all subgroups (e.g., 1-6, 2-7, 1-5, 3-6, 1, 2, 3, 4, 5, 6, and 7 carbon atoms). Nonlimiting examples of alkyl groups include, methyl, ethyl, n-propyl, isopropyl, n-butyl, sec-butyl (2-methylpropyl), t-butyl (1,1-dimethylethyl), 3,3-dimethylpentyl, and 2-ethylhexyl. Unless otherwise indicated, an alkyl group can be an unsubstituted alkyl group or a substituted alkyl group.

As used herein, the term "alkylene" refers to an alkyl group having a substituent. For example, the term "alkylene-aryl" refers to an alkyl group substituted with an aryl group. The term $C_n$ means the alkylene group has "n" carbon atoms. For example, $C_{1-6}$ alkylene refers to an alkylene group having a number of carbon atoms encompassing the entire range, as well as all subgroups, as previously described for "alkyl" groups.

As used herein, the term "cycloalkyl" refers to an aliphatic cyclic hydrocarbon group containing three to eight carbon atoms (e.g., 3, 4, 5, 6, 7, or 8 carbon atoms). The term $C_n$ means the cycloalkyl group has "n" carbon atoms. For example, $C_5$ cycloalkyl refers to a cycloalkyl group that has 5 carbon atoms in the ring. $C_{5-8}$ cycloalkyl refers to cycloalkyl groups having a number of carbon atoms encompassing the entire range (i.e., 5 to 8 carbon atoms), as well as all subgroups (e.g., 5-6, 6-8, 7-8, 5-7, 5, 6, 7, and 8 carbon atoms). Nonlimiting examples of cycloalkyl groups include cyclopropyl, cyclobutyl, cyclopentyl, cyclohexyl, cycloheptyl, and cyclooctyl. Unless otherwise indicated, a cycloalkyl group can be an unsubstituted cycloalkyl group or a substituted cycloalkyl group. The cycloalkyl groups described herein can be isolated, share a carbon atom with another cycloalkyl or heterocycloalkyl group, or fused to another cycloalkyl group, a heterocycloalkyl group, an aryl group and/or a heteroaryl group. Cycloalkyl groups can be saturated or partially unsaturated ring systems optionally substituted with, for example, one to three groups, independently selected alkyl, alkylene-OH, C(O)NH$_2$, NH$_2$, oxo (=O), aryl, haloalkyl, halo, and OH.

As used herein, the term "heterocycloalkyl" or "heterocyclic" is defined similarly as cycloalkyl, except the ring contains one to three heteroatoms independently selected from oxygen, nitrogen, or sulfur. Nonlimiting examples of heterocycloalkyl groups include piperdine, tetrahydrofuran, tetrahydropyran, dihydrofuran, morpholine, and the like. Heterocycloalkyl groups can be saturated or partially unsaturated ring systems optionally substituted with, for example, one to three groups, independently selected alkyl, alkyleneOH, C(O)NH$_2$, NH$_2$, oxo (=O), aryl, haloalkyl, halo, and OH. Heterocycloalkyl groups optionally can be further N-substituted with alkyl, hydroxyalkyl, alkylene-aryl, and alkylene-heteroaryl. The heterocycloalkyl groups described herein can be isolated, share a carbon atom with another cycloalkyl or heterocycloalkyl group, or fused to another heterocycloalkyl group, a cycloalkyl group, an aryl group and/or a heteroaryl group.

As used herein, the term "aryl" refers to monocyclic or polycyclic (e.g., fused bicyclic and fused tricyclic) carbocyclic aromatic ring systems. Examples of aryl groups include, but are not limited to, phenyl, naphthyl, tetrahydronaphthyl, phenanthrenyl, biphenylenyl, indanyl, indenyl, anthracenyl, and fluorenyl. Unless otherwise indicated, an aryl group can be an unsubstituted aryl group or a substituted aryl group.

As used herein, the term "heteroaryl" refers to monocyclic or polycyclic (e.g., fused bicyclic and fused tricyclic) aromatic ring systems, wherein one to four-ring atoms are selected from oxygen, nitrogen, or sulfur, and the remaining ring atoms are carbon, said ring system being joined to the remainder of the molecule by any of the ring atoms. Nonlimiting examples of heteroaryl groups include, but are not limited to, pyridyl, pyrazinyl, pyrimidinyl, pyrrolyl, pyrazolyl, imidazolyl, thiazolyl, tetrazolyl, oxazolyl, isooxazolyl, thiadiazolyl, oxadiazolyl, furanyl, thiophenyl, quinolinyl, isoquinolinyl, benzoxazolyl, benzimidazolyl, and benzothiazolyl. Unless otherwise indicated, a heteroaryl group can be an unsubstituted heteroaryl group or a substituted heteroaryl group.

As used herein, the term "halo" refers to a fluoro, chloro, bromo, or iodo group. The term "haloalkyl" refers to an alkyl group that is substituted with at least one halogen.

The terms "therapeutically effective amount" and "effective amount" depend on the condition of a subject and the specific compound(s) administered. The terms refer to an amount effective to achieve a desired biological, e.g., clinical effect. A therapeutically effective amount varies with the nature of the disease being treated, the length of time that activity is desired, and the age and the condition of the subject. In one aspect, a therapeutically effective amount of a compound or composition of the disclosure is an amount effective to inhibit growth of hyperproliferative cells, prevent cancer cell metastasis, and/or result in cancer cell death.

In one aspect, the present disclosure provides a compound of Formula (I), or a pharmaceutically acceptable salt thereof:

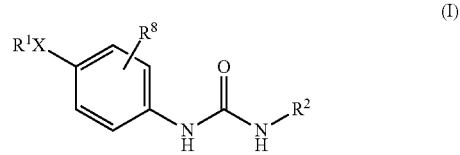

(I)

wherein: X is O, NH, or S; $R^1$ is pyridinyl, a fused bicyclic heteroaryl ring system of 9 or 10 atoms, or naphthyl, each of which is unsubstituted or substituted with 1, 2, or 3 independently selected $R^3$ groups; $R^2$ is

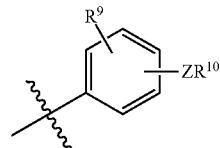

or $AR^6$; $R^3$ is halo, $C_{1-5}$ alkyl, $C_{1-5}$ haloalkyl, CONH$_2$, CONHC$_{1-5}$ alkyl, or NHCOC$_{1-5}$alkyl; A is a heterocycloalkyl or heteroaryl ring system of 5 atoms, which is substituted with $R^5$; $R^5$ is H, $C_{3-5}$ alkyl, or CF$_3$; $R^6$ is phenyl, pyridinyl, a fused bicyclic heteroaryl ring system of 9 or 10 atoms, naphthyl, or a fused bicyclic heterocycloalkyl ring system of 9 or 10 atoms, each of which is unsubstituted or substituted with 1, 2, or 3 independently selected $R^7$ groups; $R^7$ is halo, $C_{1-5}$ alkyl, $C_{1-5}$ haloalkyl, $CONH_2$, $CONHC_{1-5}$ alkyl, or $NHCOC_{1-5}$ alkyl; $R^8$ is H, halo, or $C_{1-5}$ alkyl; $R^9$ is H or $CF_3$; Z is null or $CH_2$; $R^{10}$ is a heterocycloalkyl or heteroaryl ring system of 5 or 6 atoms, which is substituted with $R^4$; and $R^4$ is H or $C_{1-3}$ alkyl. In some aspects, the compound of Formula (I) is not AST-487 or rebastinib.

In one aspect, the compound of Formula (I) has Formula (Ia):

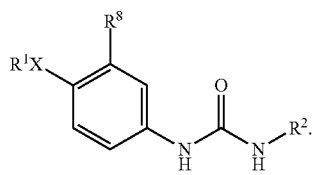

(Ia)

In another aspect, the compound of Formula (I) has Formula (Ib):

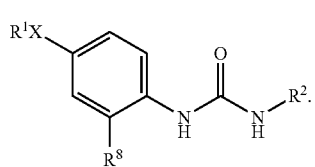

(Ib)

In Formulae (I), (Ia), and (Ib), $R^8$ is H, halo, or $C_{1-5}$ alkyl. In one aspect, $R^8$ is H. In another aspect, $R^8$ is $C_1$alkyl. In another aspect, $R^8$ is fluoro.

In Formulae (I), (Ia), and (Ib), $R^9$ is H or $CF_3$. In one aspect, $R^9$ is $CF_3$.

In Formulae (I), (Ia), and (Ib), $R^{10}$ is a heterocycloalkyl or heteroaryl ring system of 5 or 6 atoms, which is substituted with $R^4$. In one aspect, $R^{10}$ is piperazinyl, morpholinyl, pyrrolidinyl, pyrrolinyl, pyrrolyl, pyrazolidinyl, imidazolidinyl, pyrazolinyl, imidazolinyl, pyrazolyl, imidazolyl, triazolyl, tetrazolyl, piperidinyl, pyridinyl, pyridazinyl, pyrimidinyl, pyrazinyl, triazinyl, oxazolidinyl, isoxazolidinyl, thiazolidinyl, isothiazolidinyl, dioxanyl, thiomorpholinyl, or oxathianyl, each of which is substituted with $R^4$. For example, $R^{10}$ is piperazinyl, morpholinyl, or imidazolyl, each of which is substituted with $R^4$.

In Formulae (I), (Ia), and (Ib), Z is null or $CH_2$. In one aspect, Z is $CH_2$.

In Formulae (I), (Ia), and (Ib), $R^2$ is

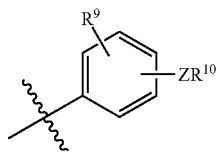

or $AR^6$. For example, $R^2$ is

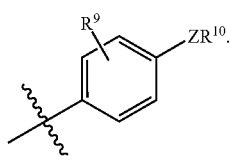

In one aspect, $R^2$ is

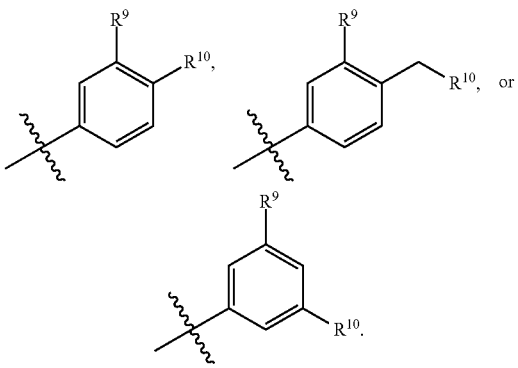

For example, $R^2$ is

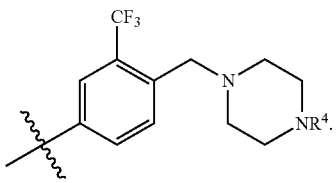

For another example, $R^2$ is

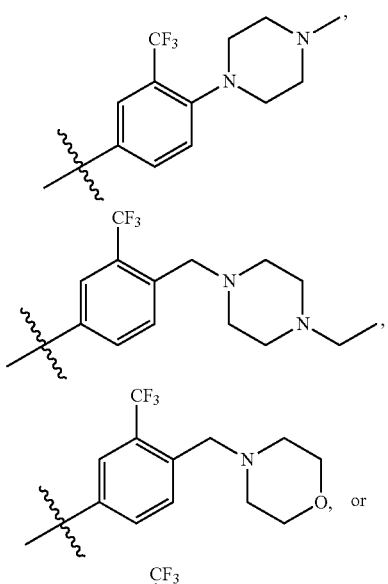

In another aspect, $R^2$ is

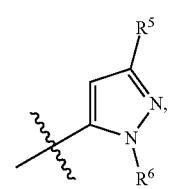

For example, $R^2$ is

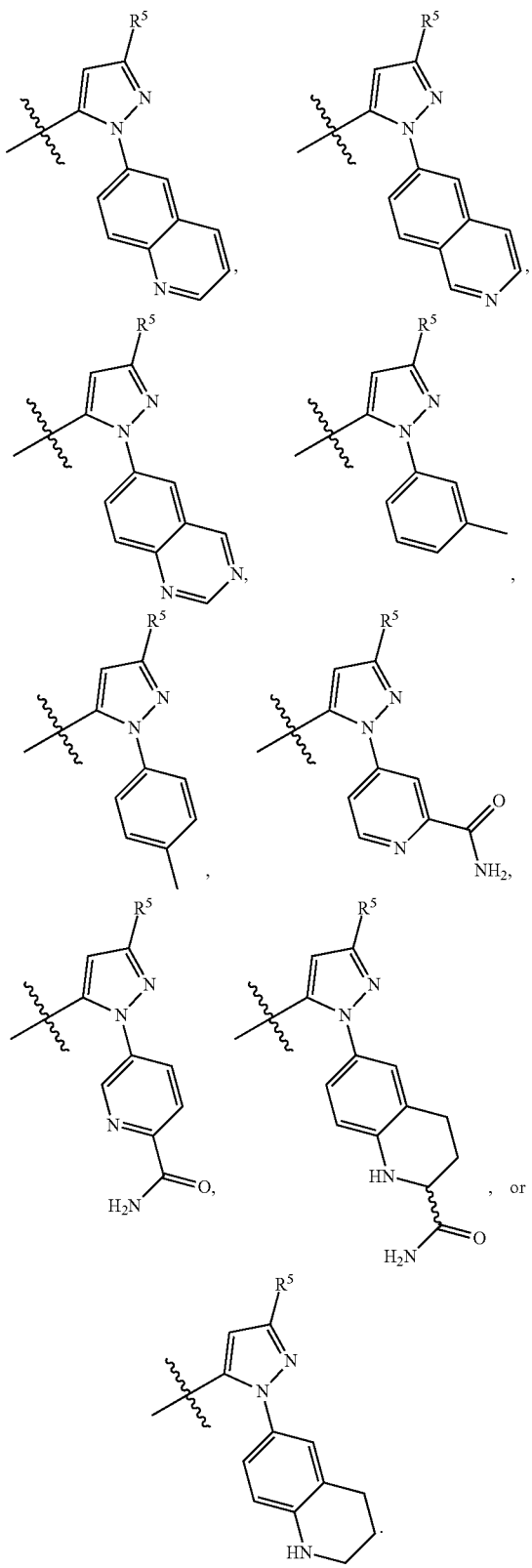

In Formulae (I), (Ia), and (Ib), $R^4$ is H or $C_{1-3}$ alkyl. In one aspect, $R^4$ is $C_1$alkyl or $C_2$alkyl.

In Formulae (I), (Ia), and (Ib), A is a heterocycloalkyl or heteroaryl ring system of 5 atoms, which is substituted with $R^5$. In one aspect, A is pyrrolidinyl, pyrrolinyl, pyrrolyl, pyrazolidinyl, imidazolidinyl, pyrazolinyl, imidazolinyl, pyrazolyl, imidazolyl, triazolyl, tetrazolyl, oxazolidinyl, isoxazolidinyl, thiazolidinyl, or isothiazolidinyl, each of which is substituted with $R^5$. For example, A is pyrazolyl, imidazolyl, or pyrrolyl, each of which is substituted with $R^5$.

In Formulae (I), (Ia), and (Ib), $R^5$ is H, $C_{3-5}$ alkyl, or $CF_3$. In one aspect, $R^5$ is $C_4$ alkyl. For example, $R^5$ can be t-butyl.

In Formulae (I), (Ia), and (Ib), $R^6$ is phenyl, pyridinyl, a fused bicyclic heteroaryl ring system of 9 or 10 atoms, naphthyl, or a fused bicyclic heterocycloalkyl ring system of 9 or 10 atoms, each of which is unsubstituted or substituted with 1, 2, or 3 independently selected $R^7$ groups. In one aspect, the fused bicyclic heteroaryl ring system of $R^6$ is quinoxalinyl, phthalazinyl, quinazolinyl, cinnolinyl, 1,8-naphthyridinyl, 1,7-naphthyridinyl, 1,6-naphthyridinyl, 1,5-naphthyridinyl, 2,7-naphthyridinyl, 2,6-naphthyridinyl, quinolinyl, or isoquinolinyl. In another aspect, the fused bicyclic heterocycloalkyl ring system of $R^6$ is indolinyl, indolyl, tetrahydroquinolinyl, dihydroquinolinyl, dihydroisoquinolinyl, or quinolizinyl. For example, $R^6$ is

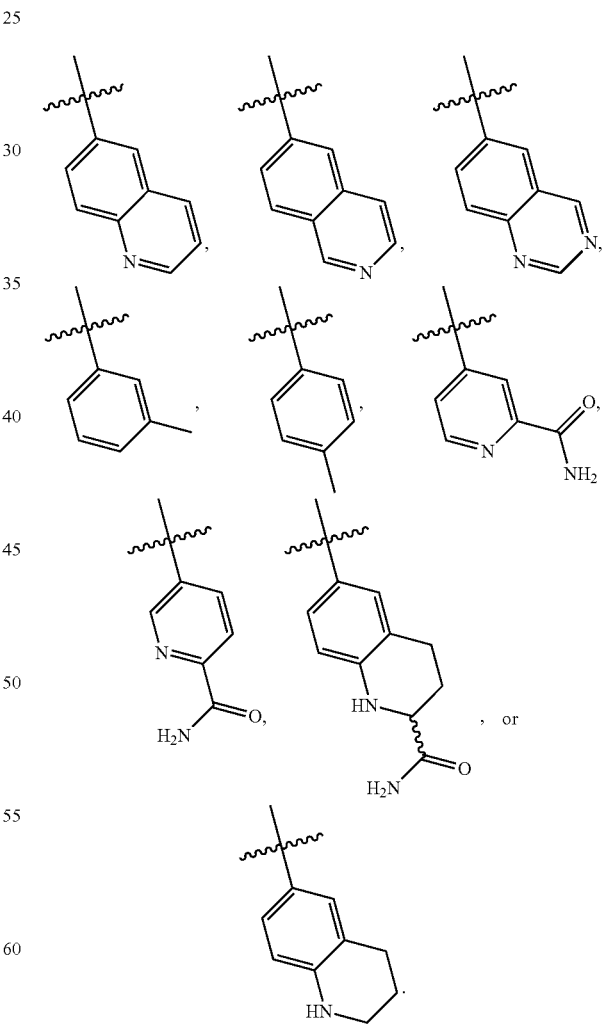

In Formulae (I), (Ia), and (Ib), $R^7$ is halo, $C_{1-5}$ alkyl, $C_{1-5}$haloalkyl, $CONH_2$, $CONHC_{1-5}$ alkyl, or $NHCOC_{1-5}$ alkyl.

In one aspect, the compound of Formula (I) has Formula (II):

(II)
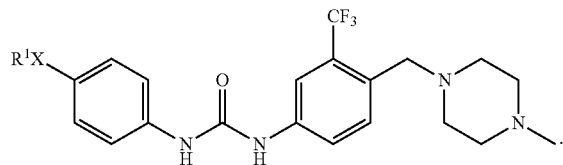

In another aspect, the compound of Formula (I) has Formula (III):

(III)
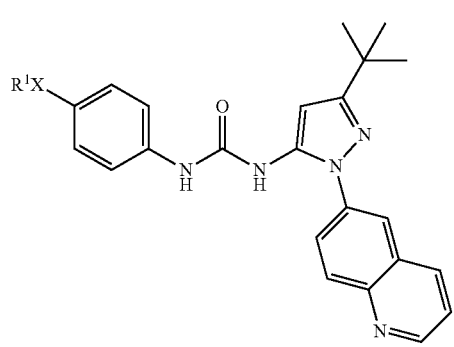

In Formulae (I), (Ia), (Ib), (II), and (III), $R^1$ is pyridinyl, a fused bicyclic heteroaryl ring system of 9 or 10 atoms, or naphthyl, each of which is unsubstituted or substituted with 1, 2, or 3 independently selected $R^3$ groups. In one aspect, the fused bicyclic heteroaryl ring system of $R^1$ is quinoxalinyl, phthalazinyl, quinazolinyl, cinnolinyl, 1,8-naphthyridinyl, 1,7-naphthyridinyl, 1,6-naphthyridinyl, 1,5-naphthyridinyl, 2,7-naphthyridinyl, 2,6-naphthyridinyl, quinolinyl, or isoquinolinyl. For example, $R^1$ can be quinazolinyl, quinolinyl, or naphthyl. In one aspect, $R^1$ is is pyridinyl or pyridinyl substituted with

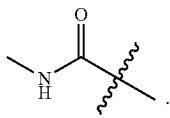 [SMILES: *C(=O)NC]

$R^1$, for example, can be selected from the group consisting of

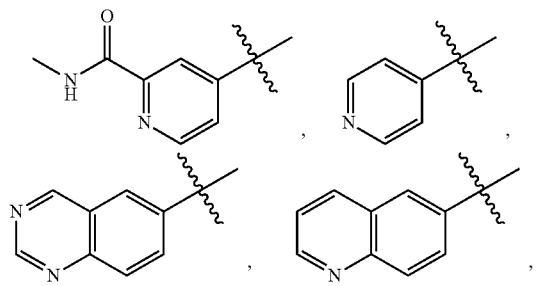

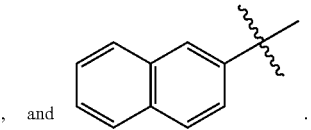

, and .

In Formulae (I), (Ia), (Ib), (II), and (III), $R^3$ is halo, $C_{1-5}$ alkyl, $C_{1-5}$haloalkyl, $CONH_2$, $CONHC_{1-5}$ alkyl, or $NHCOC_{1-5}$alkyl. In one aspect, $R^3$ is $CONHC_1$ alkyl.

In Formulae (I), (Ia), (Ib), (II), and (III), X is O, NH, or S. In one aspect, X is O. In another aspect, X is NH. In another aspect, X is S.

In some aspects, the compound of Formula (I) has a structure selected from the group consisting of:

C01
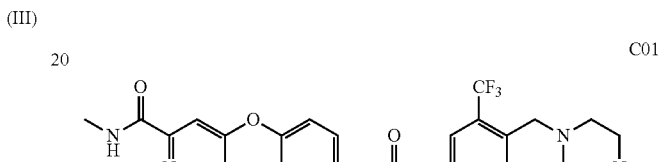

,

C02
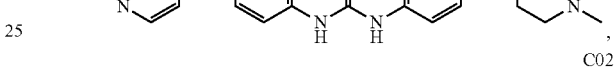

,

C03
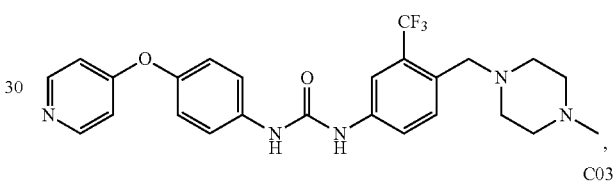

,

C04
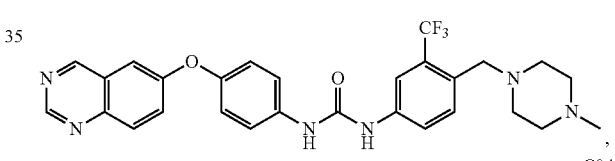

,

C05
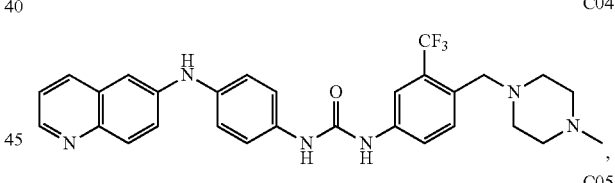

,

C06
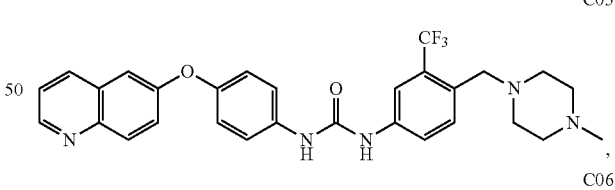

,

C07
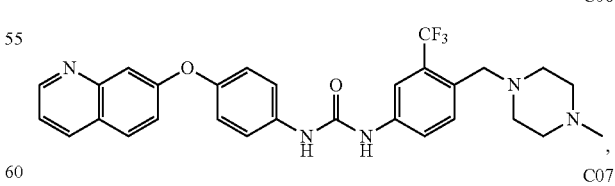

,

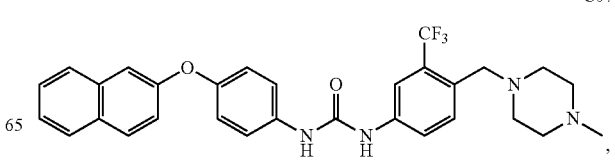

,

C08

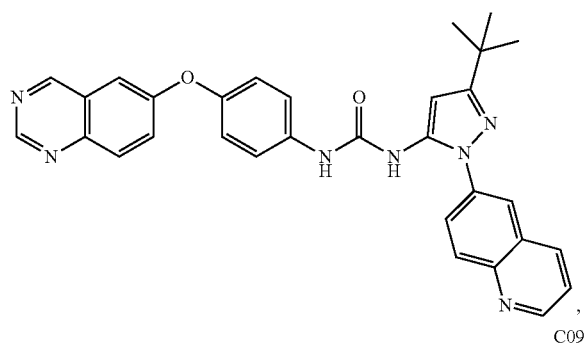

C09

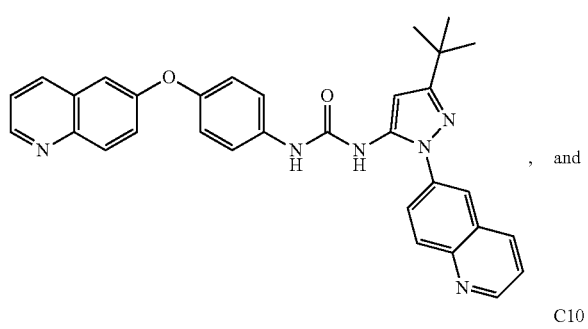
, and

C10

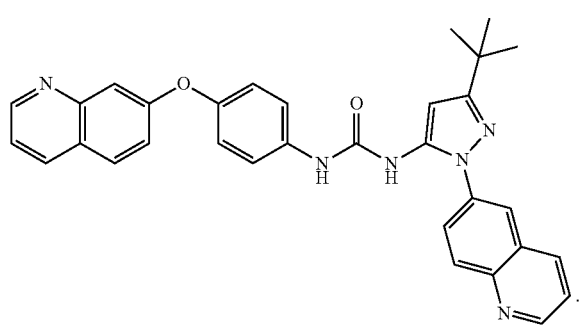

The present disclosure also provides a composition comprising a compound described herein, e.g., one or more of compounds C01 to C10 in combination with a pharmaceutically acceptable carrier. In one aspect, the composition is for use in the treatment of a hyperproliferative disease, such as chronic myelogenous leukemia. Pharmaceutically acceptable carriers include, but are not limited to, water, saline, phosphate buffered saline, and buffers. Preferably, the carrier is sterile. Other excipients, including buffering agents, dispersing agents, and preservatives, are known in the art and may be included in the composition. Further examples of components that may be employed in compositions are presented in Remington's Pharmaceutical Sciences, 16th Ed. (1980) and 20th Ed. (2000), Mack Publishing Company, Easton, Pa. A composition may be in any suitable dosage form including, but not limited to, tablets, capsules, implants, depots, liquids, patches, lozenges, creams, ointments, lotions, aerosols, and eye drops.

A method of treating a hyperproliferative disorder such as chronic myelogenous leukemia in a subject in need thereof comprises administering a therapeutically effective amount of a compound or composition described herein to the subject. In a further aspect, a method of treating cancer in a subject in need thereof also is provided comprising administering a therapeutically effective amount of a compound or composition described herein to the subject. In one aspect, a method of inhibiting cancer growth or metastasis comprising contacting a cancer cell with an effective amount of the compound or composition described herein is provided. In one aspect, a method of the present disclosure comprises administering any one of compounds C01 to C10 or a combination thereof. In any of the foregoing methods, a compound or composition described herein may be administered in an amount effective to inhibit the kinase activity of Bcr-Abl or a mutant protein thereof, such as Bcr-Abl T315I mutant protein. The ability of the compounds and compositions of the present disclosure to selectively inhibit Bcr-Abl and/or Bcr-Abl mutant protein kinase activity provides a reduction in adverse effects due to non-specific kinase inhibition. In a further aspect, the cancer is selected from a leukemia. In one aspect, the leukemia is chronic myelogenous leukemia, acute lymphoblastic leukemia, acute myelogenous leukemia, or chronic lymphocytic leukemia, optionally imatinib-resistant chronic myelogenous leukemia. One of ordinary skill will appreciate that treating a cancer does not require complete eradication of the cancer. Any beneficial physiologic response is contemplated, such as reduction in white blood cell count, reduction in cancer cell markers (e.g., amount of BCR-ABL gene in blood, presence of Philadelphia chromosome in bone marrow), reduction or halting or delay of metastasis, alleviation of symptoms and the like. In one aspect, a method of inhibiting cancer growth or metastasis comprises contacting a cancer cell with an effective amount of a compound or composition described herein.

In one aspect of the present methods, a therapeutically effective amount of a compound or composition described herein, typically formulated in accordance with pharmaceutical practice, is administered to a subject in need thereof. A particular administration regimen for a given subject will depend, in part, upon the compound or composition, the amount administered, the route of administration, and the cause and extent of any side effects. The amount administered to a subject (e.g., a mammal, such as a human) in accordance with the disclosure should be sufficient to effect the desired response over a reasonable time frame. Dosage typically depends upon the route, timing, and frequency of administration.

Purely by way of illustration, the methods of the present disclosure comprise administering, e.g., from about 0.1 mg/kg to about 150 mg/kg or more of a compound of the disclosure based on the body weight of the subject, depending on the factors mentioned above. In some aspects, the dosage ranges from about 0.1 mg/kg to about 0.5 mg/kg, about 5 mg/kg to about 75 mg/kg, about 10 mg/kg to about 50 mg/kg, about 80 mg/kg to about 120 mg/kg, about 15 mg/kg to about 30 mg/kg, about 1 mg/kg to about 20 mg/kg, or about 10 mg/kg to about 25 mg/kg. The dosage is administered as needed, for example, continuously, one to three times daily, every other day, twice a week, weekly, every two weeks, monthly, or less frequently. The treatment period will depend on the particular condition and may last one day to several days, weeks, months, or years. The above dosages are exemplary of the average case, but there can be individual instances in which higher or lower dosages are merited, and such are within the scope of this disclosure.

Suitable methods of administering a physiologically acceptable composition, such as a composition comprising a compound described herein, are well known in the art. Although more than one route can be used to administer a compound, a particular route can provide a more immediate and more effective reaction than another route. Depending on the circumstances, a composition comprising one or more compounds described herein is introduced into tumor sites, applied or instilled into body cavities, absorbed through the skin or mucous membranes, inhaled, ingested and/or introduced into circulation. In one aspect, the compound or composition is administered orally. In another aspect, the compound or composition is injected intravenously and/or intraperitoneally. In still another aspect, the compound or composition is administered locally by directly contacting cancer cells with the compound or composition. For example, in certain circumstances, it will be desirable to deliver the composition through injection or infusion by intravenous, intratumoral, intraperitoneal, intracerebral (intra-parenchymal), intracerebroventricular, intramuscular, intraocular, intraarterial, intraportal, intralesional, intramedullary, intrathecal, intraventricular, transdermal, subcutaneous, intranasal, transdermal, enteral, topical, sublingual, urethral, vaginal, or rectal means; by controlled, delayed, sustained or otherwise modified release systems; or by implantation devices. Alternatively, the composition is administered via implantation of a matrix, membrane, sponge, or another appropriate material onto which the compound has been absorbed or encapsulated. Where an implantation device is used, the device is, in one aspect, implanted into any suitable tissue or organ, and delivery of the desired compound is, for example, via diffusion, timed-release bolus, or continuous administration.

In one aspect, the compound may be attached to a targeting moiety specific for a cancer cell, such as an antigen binding protein including, but not limited to, antibodies, antibody fragments, antibody derivatives, antibody analogs, and fusion proteins, that bind a specific cancer cell antigen.

The present disclosure will be more readily understood by reference to the following examples, which are provided by way of illustration and are not intended to be limiting.

EXAMPLES

The following Examples describe the confirmation of compounds of the present disclosure as therapeutic agents.

Example 1

In Vitro Activity of Compounds C01-007 for c-Abl and c-Src

To assess the selectivity of compounds for c-Abl, the inhibitor constant ($K_1$) of each of compounds C01-C07 was measured for c-Abl and the homologous non-receptor tyrosine kinase c-Src. The hydrophobicity of each of compounds C01-C07 was also assessed by calculating the partition coefficient (c Log P), and the results are provided in Table 1.

TABLE 1

| Compound | cLogP | $K_i$, c-Abl (nM) | $K_i$, c-Src (nM) | $K_i$, c-Src/ $K_i$, c-Abl |
|---|---|---|---|---|
| C01 | 5.02 | <1 | 36 | >36 |
| C02 | 5.33 | <1 | 28 | >28 |
| C03 | 5.76 | <1 | 120 | >120 |
| C04 | 6.67 | 1.7 | 4500 | 2647 |
| C05 | 6.71 | <1 | 216 | >216 |
| C06 | 6.71 | 2 | 12000 | 6000 |
| C07 | 8.00 | 155 | >27000 | >174 |

As shown in Table 1, compounds having increased hydrophobicity generally demonstrated greater selectivity for c-Abl over c-Src. The hydrophilic pyridine-containing compounds C01 and C02, with c log P values of 5.02 and 5.33, respectively, were less than 40× selective for c-Abl over c-Src. In comparison, the more hydrophobic quinazoline- and quinoline-containing compounds C03-C06, with c log P values ranging from 5.76-6.71, were 120-6000× selective for c-Abl over c-Src. The naphthyl-containing compound C07 demonstrated nanomolar potency for c-Abl with no detectable inhibition of c-Src.

Example 2

In Vitro Activity of Compounds C01-C07 for T315I and Y253F Mutants of c-Abl

To assess the activity of compounds for the T315I and Y253F mutants of c-Abl, the inhibitor constant ($K_i$) of each of compounds C01-C07 was measured for T315I Abl and Y253F Abl. The results are provided in Table 2.

TABLE 2

| Compound | $K_i$, c-Abl (nM) | $K_i$ T315I Abl (nM) | $K_i$ Y253F Abl (nM) |
|---|---|---|---|
| C01 | <1 | <1 | <1 |
| C02 | <1 | <1 | <1 |
| C03 | <1 | <1 | <1 |
| C04 | 1.7 | 2.1 | 50 |
| C05 | <1 | <1 | <1 |
| C06 | 2 | 4 | 6.2 |
| C07 | 155 | 119 | >9000 |

As shown in Table 2, each compound demonstrated similar potency for wild type c-Abl as for the T315I Abl mutant. Compounds C01-C03, C05, and C06 also demonstrated similar potency for the Y253F Abl mutant as for the T315I Abl mutant. Compound C04 demonstrated a moderate 25× loss in potency, and compound C07 demonstrated a loss of potency.

Without wishing to be bound by theory, the Y253F mutation is believed to lead to the P-loop assuming an extended conformation due to the disruption of an H-bond between Y253 of the P-loop and N322 of the C-lobe of the kinase. This c-Src-like P-loop conformation is believed to disfavor binding of a hydrophobic hinge-binding motif due to an energetic penalty on solvation. Compounds C01-C03, C05, and C06 unexpectedly demonstrated no or minimal sensitivity to the Y253F Abl mutation, and compound C04 demonstrated only a moderate 25× loss in potency.

Example 3

Activity of Compounds C01-C06 in Wild Type and T315I Bcr-Abl Transformed Ba/F3 Cells To assess the activity of compounds in cells, the $GI_{50}$ (50% growth inhibition) of each of compounds C01-C06 was measured in wild type Bcr-Abl and T315I Bcr-Abl transformed Ba/F3 cells. As a measure of non-specific toxicity, these compounds were also tested against parental IL-3 dependent Ba/F3 cells, and the results are provided in Table 3.

TABLE 3

| Compound | $GI_{50}$, Ba/F3 wt Bcr-Abl (nM) | $GI_{50}$, Ba/F3 T315I Abl (nM) | $GI_{50}$, Ba/F3 parental (nM) |
| --- | --- | --- | --- |
| C01 | 41 | 448 | 4838 |
| C02 | 198 | 896 | 5000 |
| C03 | 214 | 75 | 5581 |
| C04 | 699 | 491 | 5117 |
| C05 | 205 | 272 | 5300 |
| C06 | 2306 | 2195 | 5224 |

As shown in Table 3, the compounds demonstrated reduced potency in both WT and T315I Bcr-Abl transformed Ba/F3 cells when compared to their biochemical potency. While the biochemical assays were carried out using the non-phosphorylated kinase domain of c-Abl, Bcr-Abl in Ba/F3 cells is in the phosphorylated state. This activated state is due to the absence of the auto-inhibitory N-myristoyl group and trans-autophosphorylation of the activation loop promoted by the oligomerization of Bcr.

Example 4

Activity of Compounds C08-C10

To assess the selectivity of compounds for c-Abl and the activity of compounds for the Y253F mutants of c-Abl, the inhibitor constant ($K_i$) of each of compounds C08-C10 was measured for c-Abl, c-Src, and Y253F Abl. To assess the activity of compounds in cells, the $GI_{50}$ (50% growth inhibition) of each of compounds C08-C10 was measured in wild type Bcr-Abl and T315I Bcr-Abl transformed Ba/F3 cells. The results are provided in Table 4.

TABLE 4

| Compound | $K_i$, c-Abl (nM) | $K_i$, Y253F Abl (nM) | $K_i$, c-Src (nM) | $GI_{50}$, Ba/F3 wt Bcr-Abl (nM) | $GI_{50}$, Ba/F3 T315I Abl (nM) |
| --- | --- | --- | --- | --- | --- |
| C08 | 0.96 | 3.4 | 518 | 44 | 4.4 |
| C09 | 0.64 | 2.5 | 143 | 674 | 316 |
| C10 | 3.3 | 7.6 | 345 | 525 | 536 |

As shown in Table 4, compounds C08-C10, demonstrated nanomolar potency against non-phosphorylated WT and Y253F Abl when tested using a biochemical assay. Additionally, the compounds were 105-540x selective for c-Abl over c-Src.

Compound C08 demonstrated only a minimal loss in potency in both WT Bcr-Abl dependent cells and T315I Bcr-Abl dependent cells when compared to its biochemical potency, and a 10x greater potency against T315I Bcr-Abl dependent cells as compared to WT Bcr-Abl dependent cells. Compounds C09 and C10 demonstrated reduced potency in both WT Bcr-Abl dependent cells and T315I Bcr-Abl dependent cells when compared to their biochemical potency.

Example 5

Activity of Compound C08 and Ponatinib in Bcr-Abl Dependent Cell Lines

To assess the efficacy of compound C08 compared to ponatinib in cells, the $GI_{50}$ (50% growth inhibition) of compound C08 and ponatinib was measured in various Bcr-Abl dependent cell lines. The results are provided in Table 5.

TABLE 5

| Compound | $GI_{50}$, Ba/F3 wt Bcr-Abl (nM) | $GI_{50}$, Ba/F3 T315I Abl (nM) | $GI_{50}$, K562 (nM) | $GI_{50}$, BV-173 (nM) | $GI_{50}$, BV-173R (nM) | Average $GI_{50}$ (nM) |
| --- | --- | --- | --- | --- | --- | --- |
| C08 | 44 | 4.4 | 21 | 2.5 | 52 | 24.8 |
| ponatinib | 53 | 45 | 2.5 | 6 | 15 | 24.3 |

As shown in Table 5, compound C08 demonstrated efficacy similar to ponatinib in Ba/F3 cells as well as the CML cell lines K562, BV-173, and BV-173R.

Example 6

Kinase Inhibition by Compound C08 and Ponatinib

To assess the selectivity of compound C08 compared to ponatinib, both compounds were screened in a single-concentration assay using the NanoSyn platform against a broad panel of 225 kinases. Compound C03 (which differs from compound C08 because it contains a trifluoromethylbenzylpiperazine tail instead of a t-butylpyrazolylquinoline tail) was also screened in the same assay to compare the effect of the t-butylpyrazolylquinoline tail on selectivity. The results are provided in Table 6.

TABLE 6

| | Screening concentration = 100 nM | | Screening concentration = 1000 nM | |
| --- | --- | --- | --- | --- |
| Compound | Percentage of kinases inhibited by 90% | Percentage of kinases inhibited by 65% | Percentage of kinases inhibited by 90% | Percentage of kinases inhibited by 65% |
| C03 | 10.2 | 18 | 21.2 | 32 |
| C08 | 4.4 | 10.4 | 18.8 | 28.4 |
| ponatinib | 18.4 | 25.6 | 27.2 | 34.8 |

As shown in Table 6, compound C08 demonstrated significantly more selectivity than ponatinib at both concentrations tested (100 nM and 1000 nM). Using a broad cutoff value of 65% inhibition of an individual kinase, compound C08 inhibited 10% of kinases in the panel versus 26% inhibited by ponatinib at 100 nM (4-fold the average $GI_{50}$ value of both compounds). The improved selectivity of compound C08 was also apparent at 1000 nM (28% compound C08 vs. 35% ponatinib) using the same cutoff value. While compound C08 was significantly more selective than compound C03 at 100 nM, the selectivity gain was more modest at a concentration of 1000 nM.

As shown in Table 7, ponatinib at a concentration of 100 nM showed complete inhibition (100%) of VEGFR 1 to 3, kinases which are believed to be responsible for the vascular toxicity of the drug. Compound C08 demonstrated significantly lower inhibition of VEGFR1 (49%), VEGFR2 (84%), and VEGFR3 (53%). Both ponatinib and compound C08 demonstrated significant inhibition of FGFR3, which has been observed to assume a kinked P-loop conformation. These data suggest that compound C08 demonstrates selectivity for enzymes with a kinked P-loop conformation over an extended P-loop conformation.

TABLE 7

| Kinase | % inhibition at 100 nM of: Compound C08 | Ponatinib | Kinase | % inhibition at 100 nM of: Compound C08 | Ponatinib |
|---|---|---|---|---|---|
| Abl1 | 97 | 100 | DDR1 | 103 | 104 |
| Tie2 | 96 | 95 | PDGFRβ | 60 | 108 |
| FGFR3 | 95 | 91 | VEGFR1 (FLT1) | 49 | 107 |
| Abl2/Arg | 93 | 99 | MAP4K5 | 8 | 102 |
| FLT3 | 92 | 95 | VEGFR2 (KDR) | 84 | 102 |
| Lyn-A | 92 | 99 | FGFR1 | 71 | 102 |
| PDGFRα | 92 | 98 | EPH-A3 | 47 | 101 |
| Lck | 91 | 99 | Csk | 76 | 100 |
| C-Raf | 98 | 118 | VEGFR3 (FLT4) | 53 | 100 |

Example 7

Pharmacokinetic Properties of Compound C08

The pharmacokinetic properties of compound C08 were characterized following intravenous (IV) bolus (at 15 mpk) or oral (PO) administration (at 30 mpk) in mice. The results are provided in Table 8.

TABLE 8

| Route | Dose (mg/kg) | $T_{1/2}$ (hr) | $AUC_{0-24}$ h (hr * ng/mL) | $Cl_{obs}$ (mL/hr/kg) | $V_{z\ obs}$ (mL/kg) | $C_{max}$ (ng/mL) | $T_{max}$ (hr) | Bioavailability (%) |
|---|---|---|---|---|---|---|---|---|
| PO | 30 | 4 | 20709.25 | 1430.6 | 8292.5 | 11850.0 | 0.5 | 25.6 |
| IV | 15 | 2.4 | 40078.4 | 374.2 | 1312.9 | N/A | N/A | N/A |

As shown in Table 8, compound C08 demonstrated a long half-life on oral administration (4 h) with a rapid onset of action (30 min) and was orally bioavailable (26%).

The foregoing Examples demonstrate that the compounds disclosed herein selectively inhibit Bcr-Abl and common mutants of Bcr-Abl, including the prevalent T315I mutant. Further, compound C08 selectively inhibits c-Abl over several closely-related kinases and shows no loss on binding to the Y253F and T315I mutants. The potency of compound C08 is maintained in vitro when targeting the activated state of the kinase. Furthermore, the selectivity profile of compound C08 is superior to that of ponatinib when screened under identical conditions. Notably, compound C08 demonstrated only weak inhibition of kinases believed to be responsible for the vascular toxicity observed with ponatinib treatment. Additionally, compound C08 is orally bioavailable with good pharmacokinetic properties.

All publications, patents and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this disclosure that certain changes and modifications may be made thereto without departing from the spirit or scope of the appended claims.

What is claimed is:

1. A compound of Formula (I), or a pharmaceutically acceptable salt thereof:

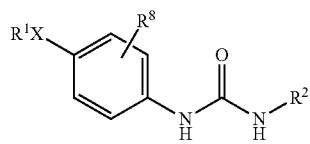

wherein:

X is O, NH, or S;

$R^1$ is quinoxalinyl, phthalazinyl, quinazolinyl, cinnolinyl, 1,8-naphthyridinyl, 1,7-naphthyridinyl, 1,6-naphthyridinyl, 1,5-naphthyridinyl, 2,7-naphthyridinyl, 2,6-naphthyridinyl, quinolinyl, isoquinolinyl, or naphthyl, each of which is unsubstituted or substituted with 1, 2, or 3 independently selected $R^3$ groups;

$R^2$ is

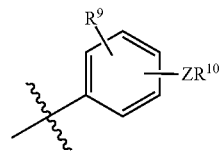

or $AR^6$;

$R^3$ is halo, $C_{1-5}$ alkyl, $C_{1-5}$ haloalkyl, $CONH_2$, $CONHC_{1-5}$ alkyl, or $NHCOC_{1-5}$ alkyl;

A is a heterocycloalkyl or heteroaryl ring system of 5 atoms, which is substituted with $R^5$;

$R^5$ is H, $C_{3-5}$ alkyl, or $CF_3$;

$R^6$ is phenyl, pyridinyl, a fused bicyclic heteroaryl ring system of 9 or 10 atoms, naphthyl, or a fused bicyclic heterocycloalkyl ring system of 9 or 10 atoms, each of which is unsubstituted or substituted with 1, 2, or 3 independently selected $R^7$ groups;

$R^7$ is halo, $C_{1-5}$ alkyl, $C_{1-5}$ haloalkyl, $CONH_2$, $CONHC_{1-5}$ alkyl, or $NHCOC_{1-5}$ alkyl;

$R^8$ is H, halo, or $C_{1-5}$ alkyl;

$R^9$ is H or $CF_3$;

Z is null or $CH_2$;

$R^{10}$ is a heterocycloalkyl or heteroaryl ring system of 5 or 6 atoms, which is substituted with $R^4$; and $R^4$ is H or $C_{1-3}$ alkyl.

2. The compound of claim 1, wherein:

$R^1$ is selected from the group consisting of

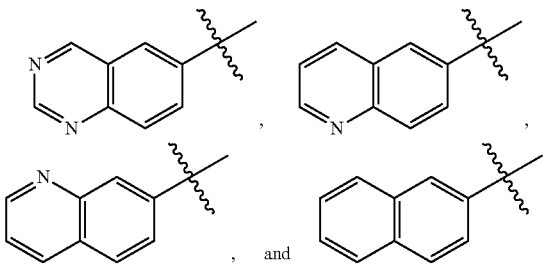

, and

.

3. The compound of claim 1, wherein $R^1$ is quinazolinyl, quinolinyl, or naphthyl.

4. The compound of claim 1, wherein:
(i) X is O; or
(ii) X is NH; or
(iii) the compound has a structure of Formula (Ia)

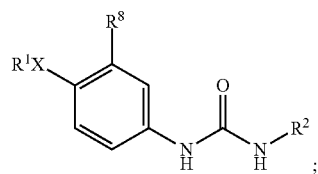

(Ia)

or
(iv) the compound has a structure of Formula (Ib)

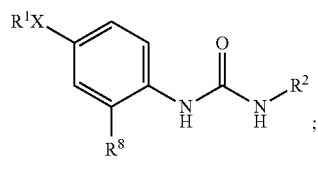

(Ib)

or
(v) $R^8$ is H, $C_1$alkyl, or fluoro.

5. The compound of claim 1, wherein
(i) $R^9$ is $CF_3$,
(ii) $R^{10}$ is piperazinyl, morpholinyl, pyrrolidinyl, pyrrolinyl, pyrrolyl, pyrazolidinyl, imidazolidinyl, pyrazolinyl, imidazolinyl, pyrazolyl, imidazolyl, triazolyl, tetrazolyl, piperidinyl, pyridinyl, pyridazinyl, pyrimidinyl, pyrazinyl, triazinyl, oxazolidinyl, isoxazolidinyl, thiazolidinyl, isothiazolidinyl, dioxanyl, thiomorpholinyl, or oxathianyl, each of which is substituted with $R^4$,
(iii) Z is $CH_2$,
(iv)

$R^2$ is

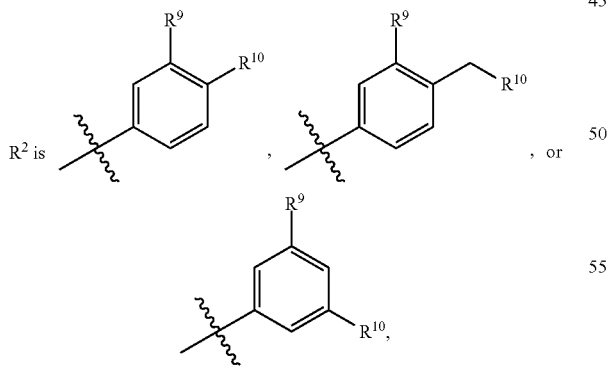

, or or
(v) $R^4$ is $C_1$alkyl or $C_2$alkyl.

6. The compound of claim 1, wherein A is pyrrolidinyl, pyrrolinyl, pyrrolyl, pyrazolidinyl, imidazolidinyl, pyrazolinyl, imidazolinyl, pyrazolyl, imidazolyl, triazolyl, tetrazolyl, oxazolidinyl, isoxazolidinyl, thiazolidinyl, or isothiazolidinyl, each of which is substituted with $R^5$.

7. The compound of claim 6, wherein A is pyrazolyl, imidazolyl, or pyrrolyl, each of which is substituted with $R^5$.

8. The compound of claim 1, wherein $R^6$ is (i) quinoxalinyl, phthalazinyl, quinazolinyl, cinnolinyl, 1,8-naphthyridinyl, 1,7-naphthyridinyl, 1,6-naphthyridinyl, 1,5-naphthyridinyl, 2,7-naphthyridinyl, 2,6-naphthyridinyl, quinolinyl, or isoquinolinyl or (ii) indolinyl, indolyl, tetrahydroquinolinyl, dihydroquinolinyl, dihydroisoquinolinyl, or quinolizinyl.

9. The compound of claim 1, wherein $R^6$ is

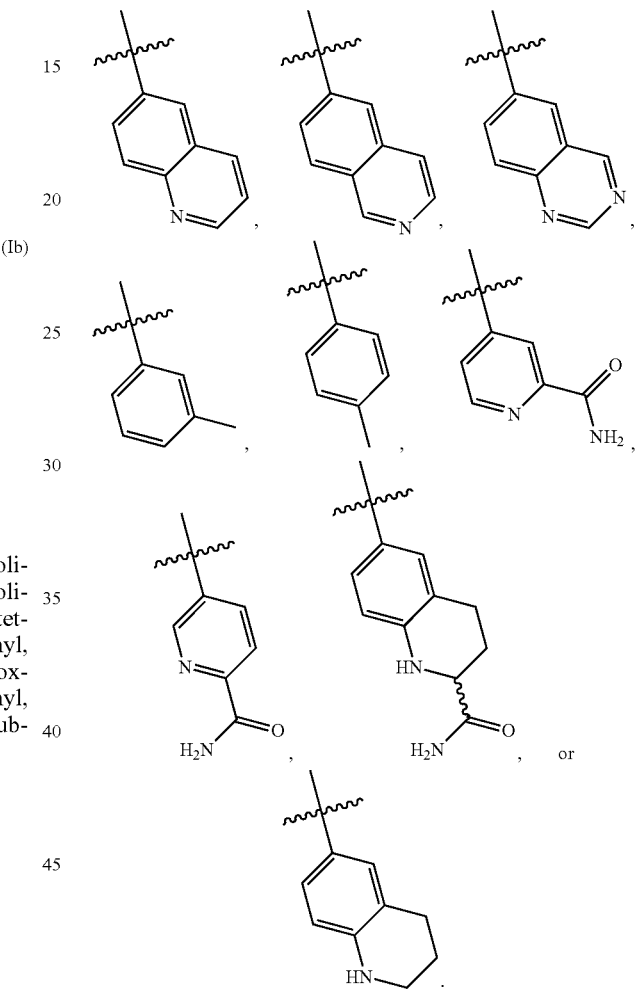

10. The compound of claim 1, wherein $R^2$ is

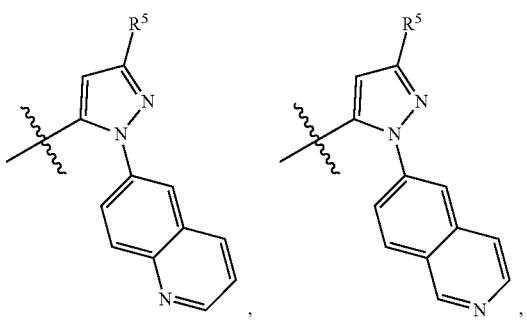

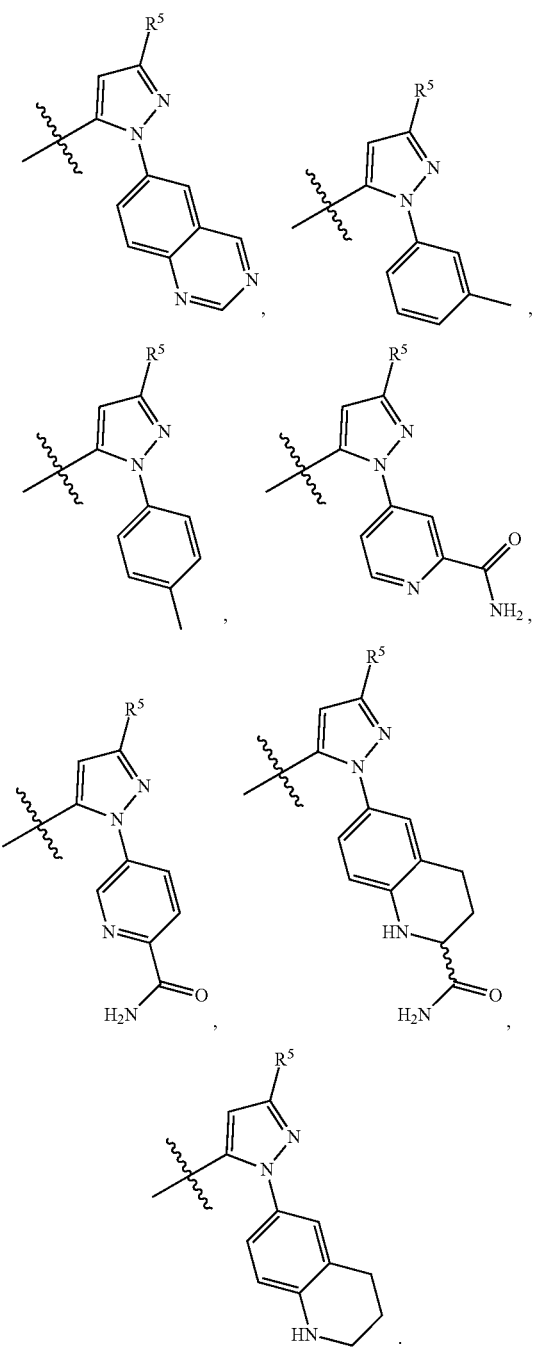
11. The compound of claim 1, having a structure of Formula (II) or Formula (III):
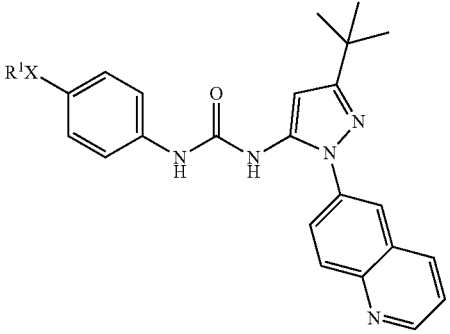
12. The compound of claim 1, wherein $R^{10}$ is piperazinyl, morpholinyl, or imidazolyl, each of which is substituted with $R^4$.
13. The compound of claim 1, wherein
$R^2$ is 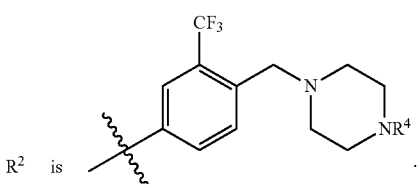
14. The compound of claim 1, wherein
$R^2$ is 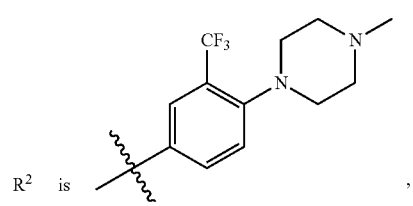
, 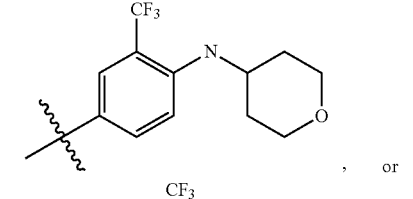
15. A compound having a structure selected from the group consisting of

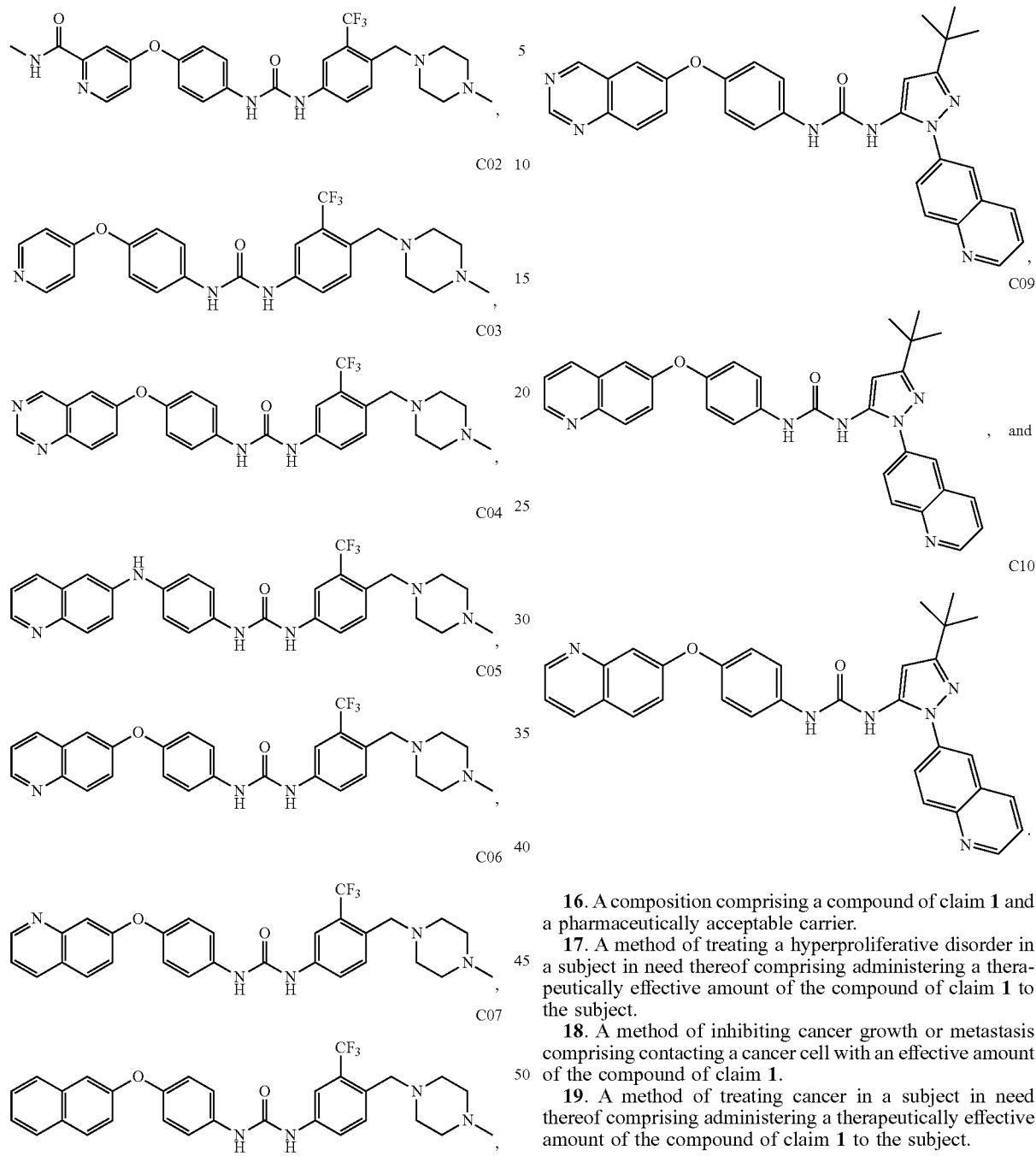

16. A composition comprising a compound of claim 1 and a pharmaceutically acceptable carrier.

17. A method of treating a hyperproliferative disorder in a subject in need thereof comprising administering a therapeutically effective amount of the compound of claim 1 to the subject.

18. A method of inhibiting cancer growth or metastasis comprising contacting a cancer cell with an effective amount of the compound of claim 1.

19. A method of treating cancer in a subject in need thereof comprising administering a therapeutically effective amount of the compound of claim 1 to the subject.

* * * * *